United States Patent
Cai et al.

(10) Patent No.: US 8,931,627 B2
(45) Date of Patent: Jan. 13, 2015

(54) BOTTLE PUSHING MECHANISM FOR TUNNEL TYPE STERILIZING DRYER

(75) Inventors: Dayu Cai, Changsha (CN); Zhen Liu, Changsha (CN); Zhigao Ning, Changsha (CN); Zanming Zhu, Changsha (CN); Bo Yi, Changsha (CN); Pengcheng Li, Changsha (CN); Yue Tang, Changsha (CN)

(73) Assignee: Truking Technology Limited, Changsha, Hunan Province (CN)

( * ) Notice: Subject to any disclaimer, the term of this patent is extended or adjusted under 35 U.S.C. 154(b) by 177 days.

(21) Appl. No.: 13/636,052

(22) PCT Filed: Jun. 24, 2010

(86) PCT No.: PCT/CN2010/074439
§ 371 (c)(1),
(2), (4) Date: Sep. 19, 2012

(87) PCT Pub. No.: WO2011/120259
PCT Pub. Date: Oct. 6, 2011

(65) Prior Publication Data
US 2013/0034418 A1    Feb. 7, 2013

(30) Foreign Application Priority Data
Mar. 30, 2010   (CN) .......................... 2010 1 0135584

(51) Int. Cl.
*B65G 19/24*    (2006.01)
*B65B 55/02*    (2006.01)
*B65B 35/44*    (2006.01)
*A61L 2/06*    (2006.01)

(52) U.S. Cl.
CPC ............... *B65B 55/025* (2013.01); *B65B 35/44* (2013.01); *A61L 2/06* (2013.01); *A61L 2202/23* (2013.01)
USPC ............................ 198/731; 198/429; 198/817

(58) Field of Classification Search
CPC ........... B65G 17/42; B65G 2201/0244; B65G 47/082
USPC .......... 198/429, 430, 817, 850, 853, 717–733
See application file for complete search history.

(56) References Cited

U.S. PATENT DOCUMENTS

| | | | | |
|---|---|---|---|---|
| 1,688,368 A | * | 10/1928 | Walker | 198/732 |
| 3,917,053 A | * | 11/1975 | Matsuyama | 198/718 |
| 5,546,734 A | * | 8/1996 | Moncrief et al. | 198/731 |
| 5,711,412 A | * | 1/1998 | Gysin et al. | 198/732 |
| 2002/0043446 A1 | * | 4/2002 | Guglielmo et al. | 198/611 |

* cited by examiner

*Primary Examiner* — James R Bidwell

(57) ABSTRACT

A bottle pushing mechanism for a tunnel type sterilizing dryer, includes a bottle pushing block (2) and at least one barb (5) cooperated with meshes of a transmitting mesh belt (1). The barb (5) is connected with the bottle pushing block (2). The bottle pushing block (2) could move along with the transmitting mesh belt (1) by the barb (5). The bottle pushing mechanism has a simple and compact structure, convenient installation, high reliability, good transmitting effect and no pollution.

5 Claims, 8 Drawing Sheets

BOTTLE PUSHING MECHANISM FOR TUNNEL TYPE STERILIZING DRYER

CROSS REFERENCE OF RELATED APPLICATION

This is a U.S. National Stage under 35 USC 371 of the International Application PCT/CN2010/074439, filed on Jun. 24, 2010.

BACKGROUND OF THE PRESENT INVENTION

1. Field of Invention

The present invention relates to a field of mechanical equipment for packaging of food, medicine, and etc., and more particularly to a tunnel type sterilizing dryer.

2. Description of Related Arts

Tunnel type sterilizing dryers are frequently adopted in industry of packaging machinery for food, pharmacy and etc. Taking pharmacy packaging machinery as an example, transmitting mesh belt is usually adopted in a tunnel type sterilizing dryer to transmit medicine bottles. When a tunnel drying oven is handing over with other equipments, a transition plate is often adopted for connecting. The medicine bottle is transmitted on the transition plate by friction driving. If a large number of medicine bottles are in the tunnel type sterilizing dryer, sufficient friction thrust can be supplied to push the bottles on the transition plate. However, when the process is completed, as the number of medicine bottles on the transmitting mesh belt of the dryer decreasing, the friction thrust that promotes medicine bottles on the transition plate decreases accordingly. When the friction between the mesh belt and a bottom of the medicine bottle is less than the friction while the medicine bottle is on the transition plate, sliding friction occurs between the mesh belt and the bottom of the medicine bottle. Thus, small number of medicine bottles always remain on the transmitting mesh belt and the transition plate in the end. If the medicine bottles are pushed out in a manual way, the sterilized medicine bottles are contaminated again. If a bottle pushing plate having big weight is provided at the end line of the medicine bottles to promote the medicine bottles, the medicine bottles can be pushed out from the dryer. However, due to the big weight and bad heating effect of the bottle pushing plate, it is difficult to sterilize or eliminate pyrogen from the bottle pushing plate. So after entering a cooling space, the bottle pushing plate contaminates the sterilized medicine bottles. Further more, friction between the medicine bottles and the transition plate generates dust or particles polluting the environment, and also generates scratches at the bottom of the medicine bottle, which have a bad effect on the appearance quality of the medicine bottles.

SUMMARY OF THE PRESENT INVENTION

In view of technical problems in existing technology, the present invention provides a bottle pushing mechanism for a tunnel type sterilizing dryer which has a simple and compact structure, convenient installation, high reliability, good transmitting effect and no pollution.

In order to solve the technical problem mentioned above, technical solutions adopted by the present invention are as following.

A bottle pushing mechanism for a tunnel type sterilizing dryer is characterized in comprising a bottle pushing block and at least one barb cooperated with meshes of a transmitting mesh belt, wherein the barb is connected with the bottle pushing block, the bottle pushing block moves along with the transmitting mesh belt by the barb.

Further improvement provided by the present invention is as following.

A middle portion of the barb is hinged on the bottle pushing block. A first end of the barb is connected with a first end of a tension spring, and a second end of the tension spring is fixed on the bottle pushing block.

The tension spring is connected with the bottle pushing block via a nut pin and an adjusting screw, wherein a threaded hole is provided on a side of the nut pin, a first end of the adjusting screw is fixed on the bottle pushing block, and a second end of the adjusting screw is sleeved in the threaded hole.

One end of the barb which is cooperated with the meshes is an inverted triangle in shape.

Compared with the prior art, advantages of the present invention are following.

1. The bottle pushing mechanism for the tunnel type sterilizing dryer, according to preferred embodiments of the present invention, is capable of achieving pushing the medicine bottles merely by bottle pushing blocks hitched on the transmitting mesh belt, and thus has advantages of simple and compact structure, convenient installation, high reliability, and good transmitting effect.

2. In the bottle pushing mechanism for the tunnel type sterilizing dryer according to preferred embodiments of the present invention, hinge connection is designed between the barb and the bottle pushing block. When meeting a resistance or moving to the transition plate, situation of crushing bottles or damaging other parts is avoided, which significantly improves reliability thereof.

Figure 1:
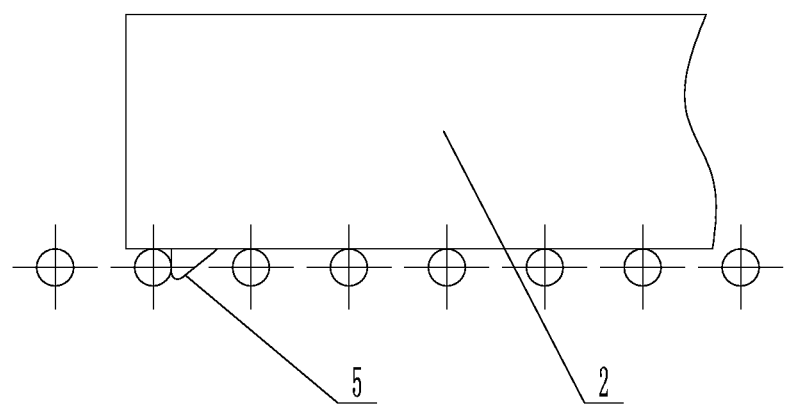
FIG. 1 is a structural schematic view according to a preferred embodiment 1 of the present invention.

Number of elements in the drawings is as following.

1—transmitting mesh belt; 2—bottle pushing block; 3—medicine bottle; 4—transition plate; 5—barb; 6—tension spring; 7—nut pin; 71—threaded hole; 8—adjusting screw

DETAILED DESCRIPTION OF THE PREFERRED EMBODIMENT

These and other objectives, features, and advantages of the present invention will become apparent from the following detailed description, the accompanying drawings, and the appended claims.

Figure 5:
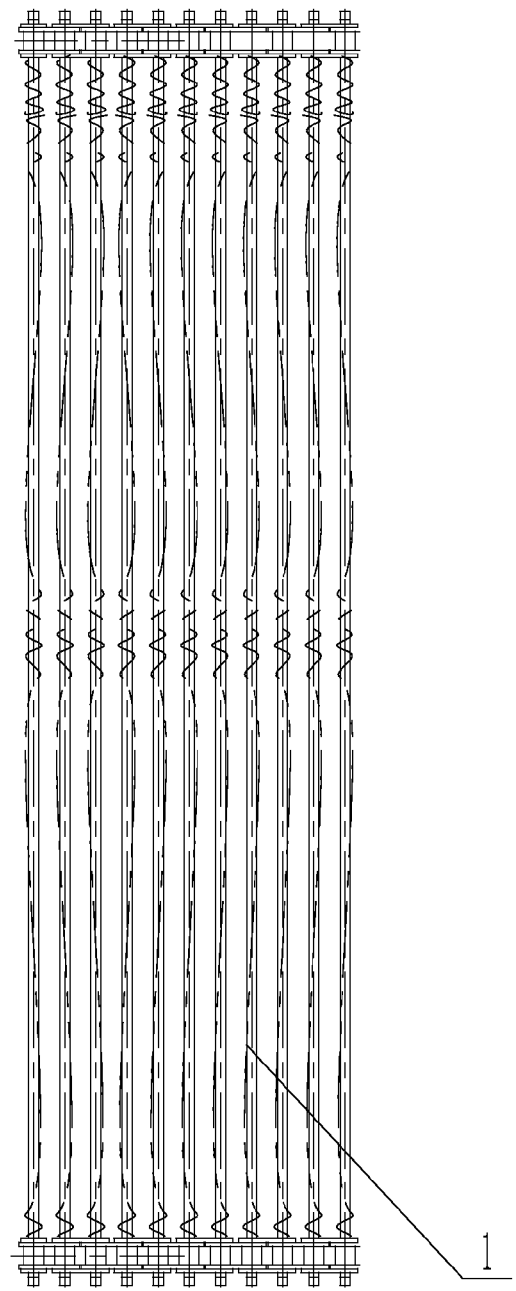
FIG. 5 is a structural schematic view of a transmitting mesh belt.

Referring to FIG. 1 and FIG. 5 of the drawings, a bottle pushing mechanism for a tunnel type sterilizing dryer according to a preferred embodiment 1 of the present invention is illustrated, comprises a bottle pushing block 2 and at least one barb 5 cooperated with meshes of the transmitting mesh belt 1. The barb 5 is connected with the bottle pushing block 2, and the bottle pushing block 2 moves along with the transmitting mesh belt 1 by the barb 5. In the preferred embodiment 1, the barb 5 is fixedly connected with the bottle pushing block 2. When the transmitting mesh belt 1 moves forward, the meshes of the transmitting mesh belt 1 pulls the barb 5 to drive the bottle pushing block 2, so the bottle block 2 push the medicine bottle 3 to move forward accordingly.

Because the barb 5 is fixedly connected with the bottle pushing block 2, when the bottle pushing block 2 is blocked, the barb 5 is stuck in the transmitting mesh belt 1; and when the resistance is over large, the meshes of the transmitting mesh belt 1 are probably damaged. Thus, technical solutions of a preferred embodiment 2 are further provided.

Figure 2:
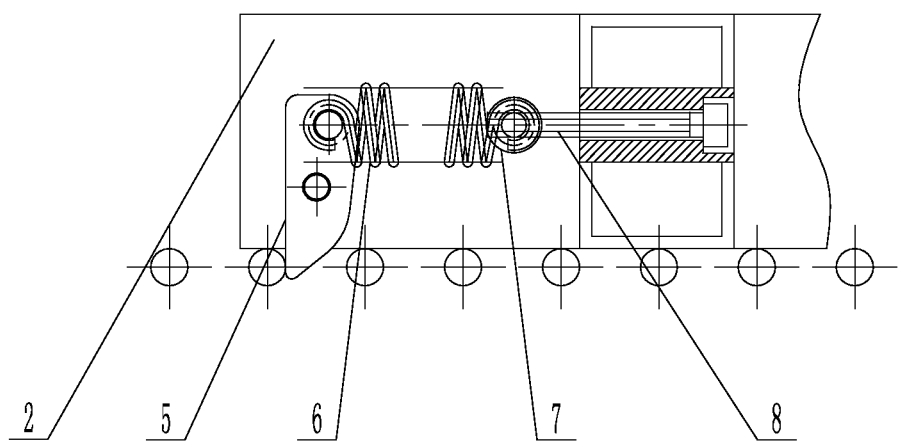
FIG. 2 is a front schematic view according to a preferred embodiment 2 of the present invention.
Figure 3:
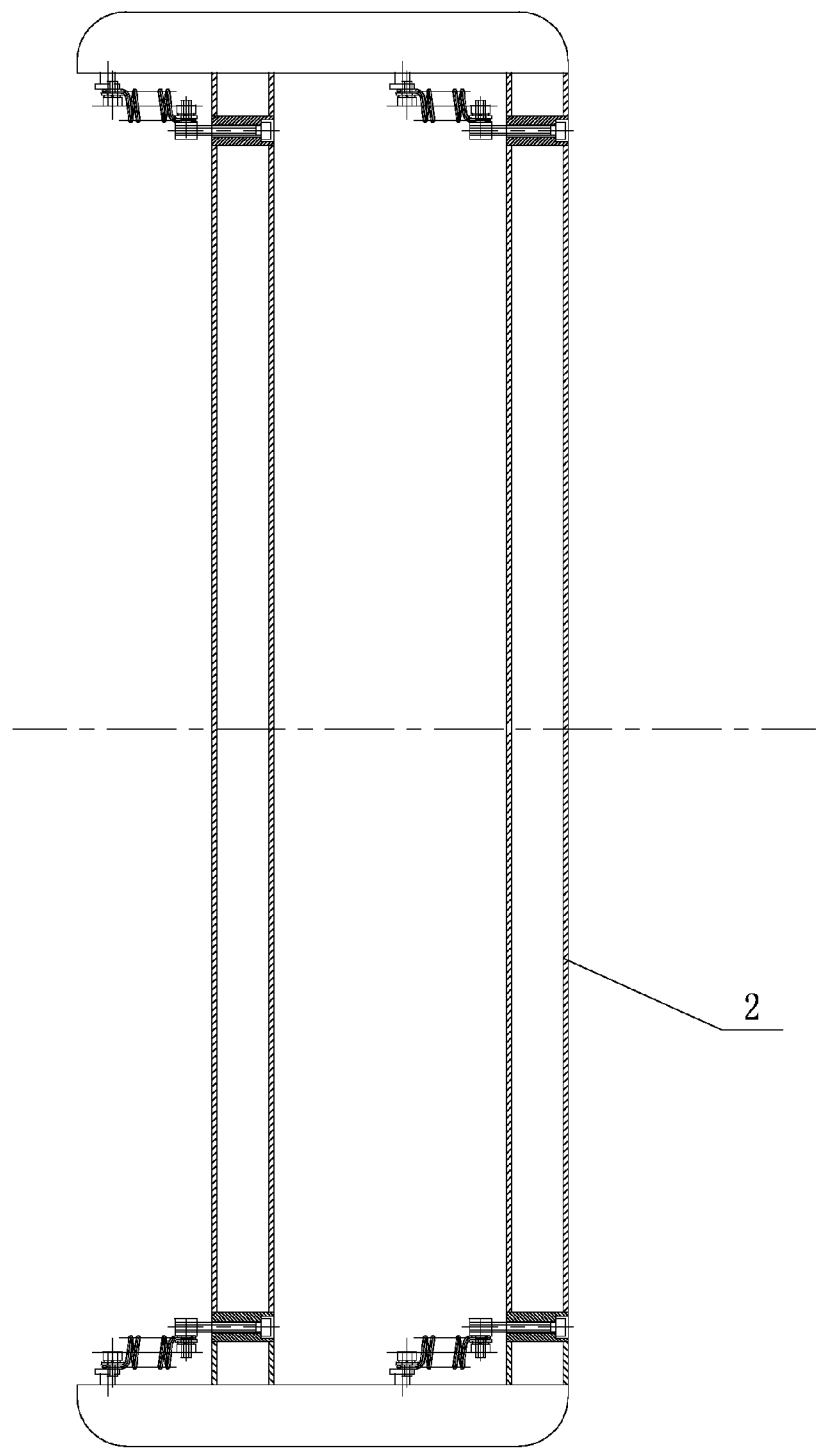
FIG. 3 is a top schematic view according to the preferred embodiment 2 of the present invention.
Figure 4:
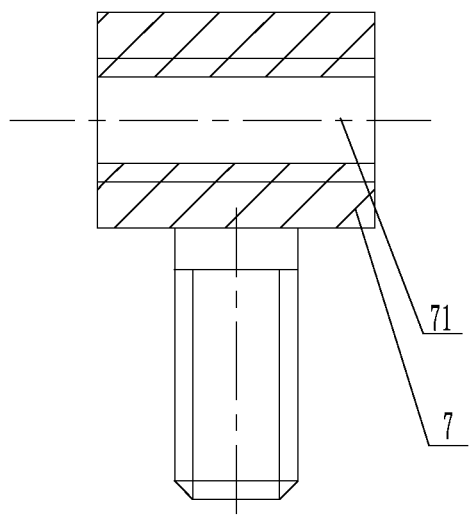
FIG. 4 is a sectional schematic view of a nut pin according to the preferred embodiment 2 of the present invention.

Referring to FIG. 2, FIG. 3, and FIG. 4 of the drawings, in the preferred embodiment 2, a middle portion of the barb 5 is hinged on the bottle pushing block 2. The barb 5 is capable of rotating around a hinge point thereof. A working end of the barb 5 is cooperated with the meshes, and a non-working end of the barb 5 is connected with a first end of a tension spring 6 via a bolt. A second end of the tension spring 6 is fixed on the bottle pushing block 2. The tension spring 6 is connected with the bottle pushing block 2 via a nut pin 7 and an adjusting screw 8. A threaded hole 71 is provided on a side of the nut pin 7. A first end of the adjusting screw 8 is fixed on the bottle pushing block 2, and a second end of the adjusting screw 8 is sleeved in the threaded hole 71. The adjusting screw 8 is capable of adjusting a position of the nut pin 7 according to needed tightness of the tension spring 6, so as to adjust tension strength of the tension spring 6. The working end of the barb 5 is cooperated with the meshes and in a shape of an inverted triangle, in such a manner that the bottle pushing block 2 bears a counter thrust from the transition plate 4 while reaching the transition plate 4, and automatically rotates back clockwise, in such a manner that the bottle pushing block 2 is capable of reaching the transition plate 4. The bottle pushing block 2 is chamfered in periphery, so as to prevent the bottle pushing block 2 from hitching a baffle at a lateral side while being on the transmitting mesh belt 1.

Figure 6:
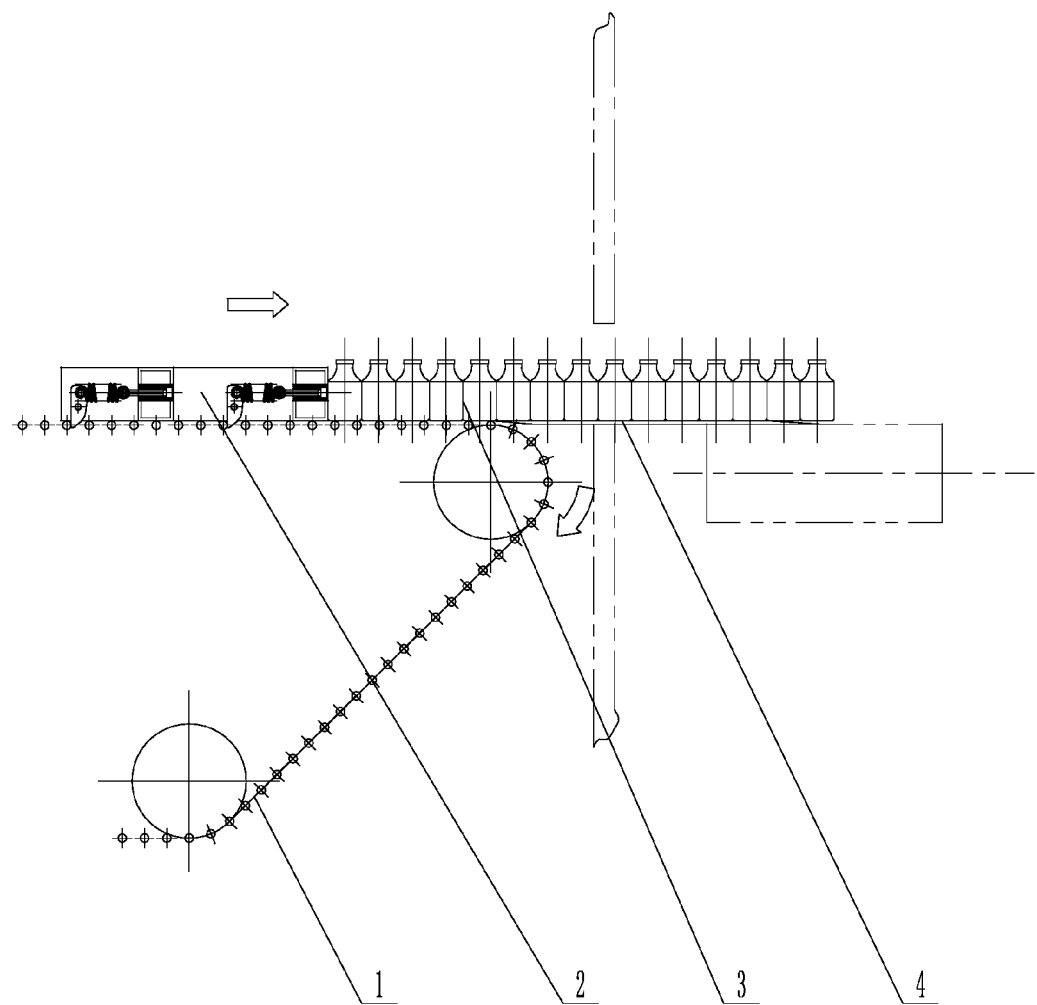
FIG. 6 is a structural schematic view of a particular application according to the preferred embodiment 2 of the present invention.
Figure 7:
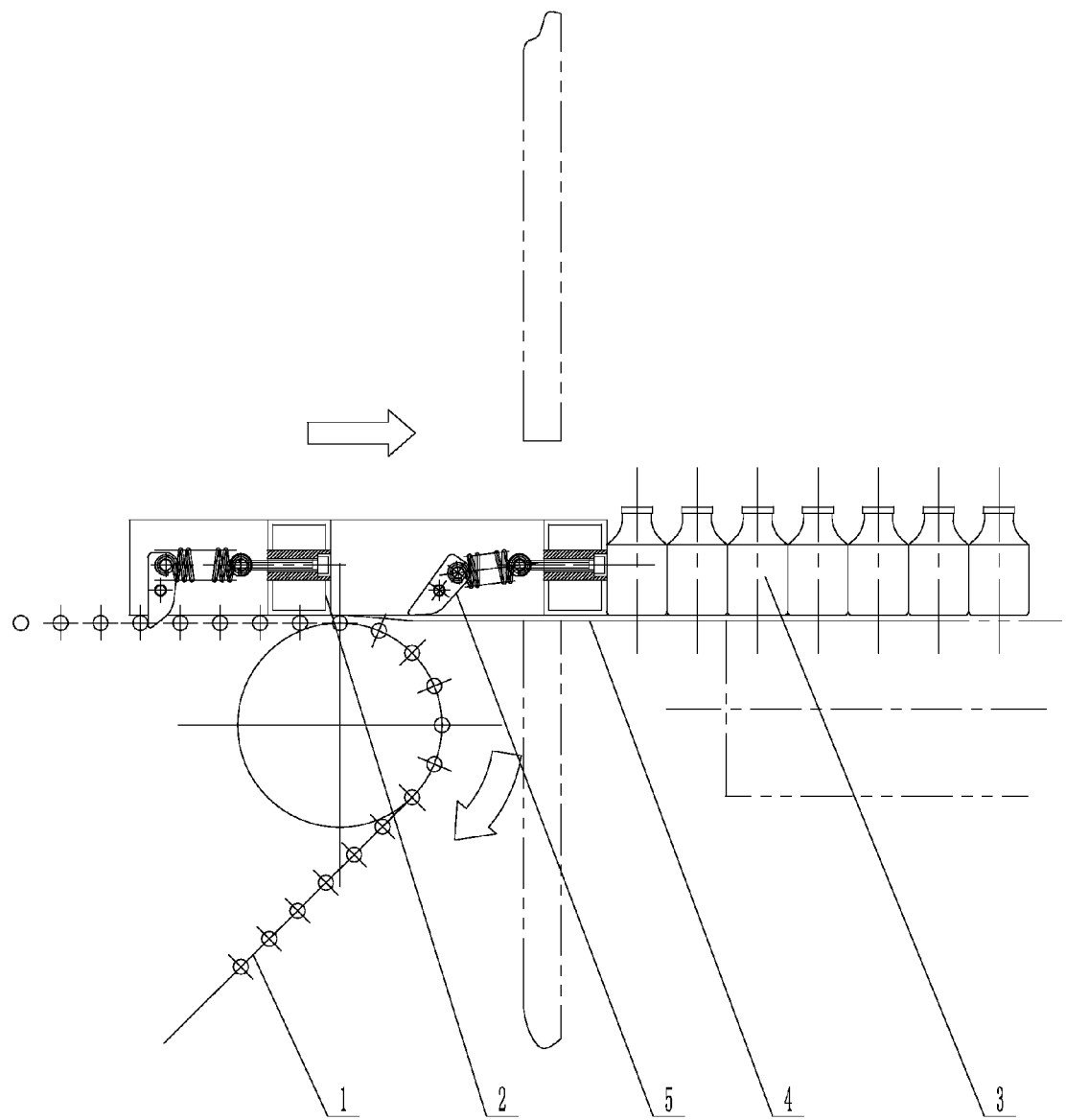
FIG. 7 is a structural schematic view of a particular application according to the preferred embodiment 2 of the present invention, showing a situation that bottles are pushed to a transition plate.
Figure 8:
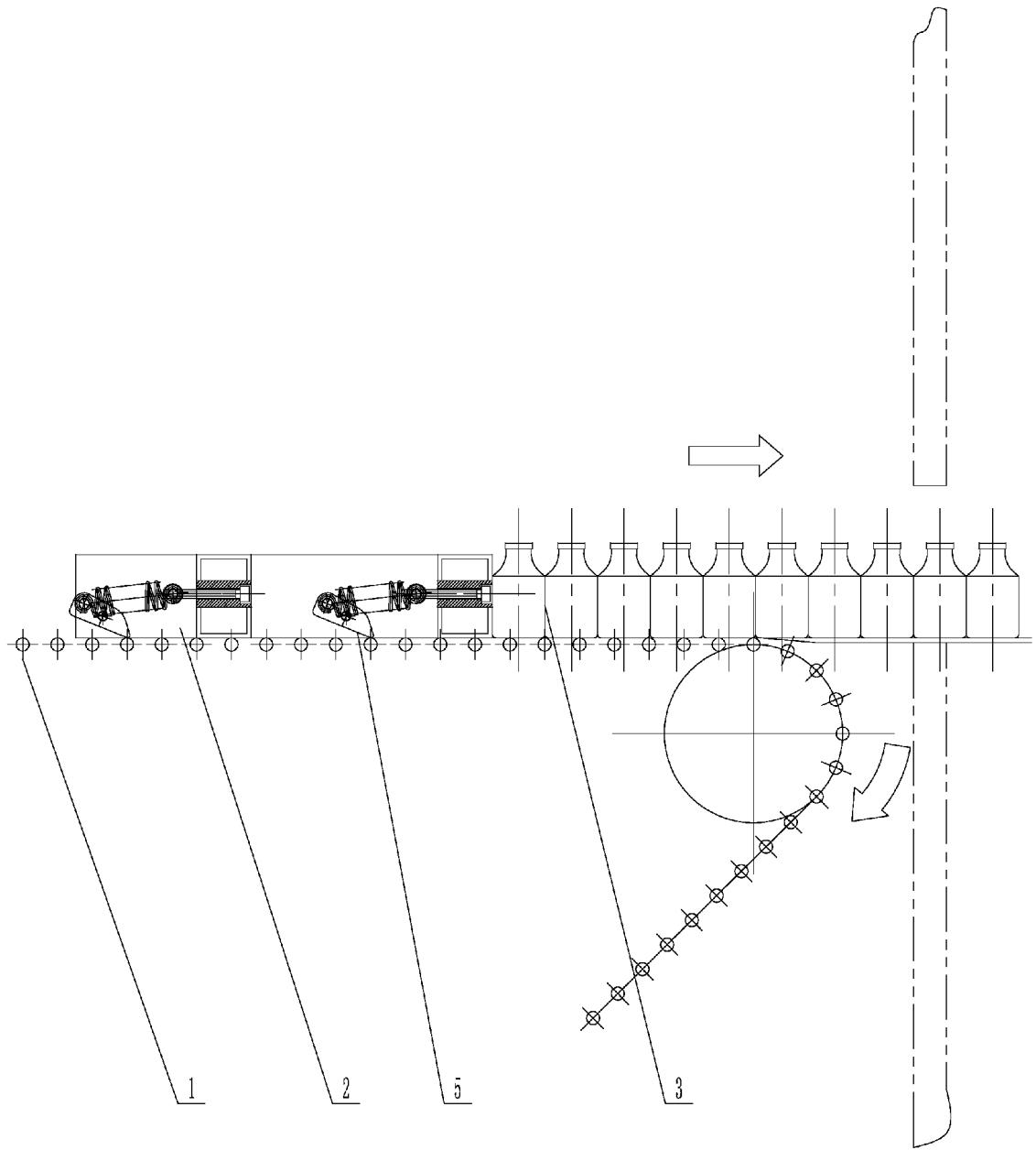
FIG. 8 is a structural view of a particular application according to the preferred embodiment 2 of the present invention, showing a situation when jamming occurs.

Referring to FIG. 6 of the drawings, direction of an arrow is the moving direction of the transmitting mesh belt 1. When production is finished, at least one of the bottle pushing block 2 is laid against a back of a last line of the medicine bottles 3, and is provided on the transmitting mesh belt 1 of the tunnel type sterilizing dryer. The barb 5 of the bottle pushing block 2 is inserted between meshes of the transmitting mesh belt 1. Previous moving thrust of the transmitting mesh belt 1 pulls the barb 5 inserted in the meshes of the transmitting mesh belt 1 to push the bottle pushing block 2, so as to achieve an object of pushing the last line of the medicine bottles 3 with the bottle pushing block 2 having a light weight. Referring to FIG. 7 of the drawings, the bottle pushing block 2 bears a counter thrust from the transition plate 4 while reaching the transition plate 4, and automatically rotates back clockwise. Referring to FIG. 8 of the drawings, when the transition plate 4 or the medicine bottle 3 is bearing a strong resistance, as the barb 5 is inserted in the meshes of the transmitting mesh belt 1, the transmitting mesh belt 1 moves forward driven by a motor. If tension of the bottle pushing block 2 is not released, the bottle pushing block 2 will crush the medicine bottles 3 ahead of the bottle pushing block 2 or scratch mechanical parts. A tension spring 6 is provided on an upper portion of the barb 5 to provide a pulling force. When jamming occurs, and the thrust provide by the transmitting mesh belt 1 is greater than pulling force of the tension spring 6 on the barb 5, the tension spring 6 stretches and the barb 5 rotates counterclockwise, so as to prevent scratching the mesh belt or crushing the medicine bottle 3.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A bottle pushing mechanism for a tunnel type sterilizing dryer, comprising: a bottle pushing block and at least one barb cooperated with meshes of a transmitting belt, wherein said barb is connected with said bottle pushing block, said bottle pushing block could move along with said transmitting mesh belt by said barb, wherein a middle portion of said barb is hinged on said bottle pushing block, one end of said barb is connected with a first end of a tension spring, and a second end of said tension spring is fixed on said bottle pushing block.

2. The bottle pushing mechanism for the tunnel type sterilizing dryer, as recited in claim 1, wherein said tension spring is connected with said bottle pushing block via a nut pin and an adjusting screw, wherein a threaded hole is provided on a side of said nut pin, a first end of said adjusting screw is fixed on said bottle pushing block, and a second end of said adjusting screw is sleeved in said threaded hole.

3. The bottle pushing mechanism for the tunnel type sterilizing dryer, as recited in claim 2, wherein one end of said barb which is cooperated with said meshes is an inverted triangle in shape.

4. The bottle pushing mechanism for the tunnel type sterilizing dryer, as recited in claim 1, wherein one end of said barb which is cooperated with said meshes is an inverted triangle in shape.

5. A bottle pushing mechanism for a tunnel type sterilizing dryer, comprising: a bottle pushing block and at least one barb cooperated with meshes of a transmitting belt, wherein said barb is connected with said bottle pushing block, said bottle pushing block could move along with said transmitting mesh belt by said barb, wherein one end of said barb which is cooperated with said meshes is an inverted triangle in shape.

\* \* \* \* \*